United States Patent
Zoppetti et al.

(10) Patent No.: US 7,268,122 B2
(45) Date of Patent: Sep. 11, 2007

(54) USE OF OVERSULFATED POLYSACCHARIDES AS INHIBITORS OF HIV

(75) Inventors: Giorgio Zoppetti, Via Mac Mahon, 43, Milan I-20155 (IT); Pasqua Anna Oreste, Milan (IT); Guido Poli, Segrate (IT); Elisa Vicenzi, Segrate (IT)

(73) Assignees: Fondazione Centro San Raffaele Del Monte Tabor, Milan (IT); Giorgio Zoppetti, Milan (IT); Pasqua Oreste, Milan (IT)

( * ) Notice: Subject to any disclaimer, the term of this patent is extended or adjusted under 35 U.S.C. 154(b) by 239 days.

(21) Appl. No.: 10/484,883

(22) PCT Filed: Jul. 26, 2002

(86) PCT No.: PCT/IB02/02909

§ 371 (c)(1),
(2), (4) Date: Aug. 18, 2004

(87) PCT Pub. No.: WO03/011307

PCT Pub. Date: Feb. 13, 2003

(65) Prior Publication Data

US 2005/0009780 A1  Jan. 13, 2005

(30) Foreign Application Priority Data

Jul. 27, 2001 (IT) .......................... MI2001A1633

(51) Int. Cl.
*A61K 31/737* (2006.01)
(52) U.S. Cl. ....................................................... 514/54
(58) Field of Classification Search ................... 514/54
See application file for complete search history.

(56) References Cited

U.S. PATENT DOCUMENTS

| 5,384,398 A | 1/1995 | Lormeau et al. |
| 6,992,183 B2 * | 1/2006 | Oreste et al. ............ 536/123.1 |

FOREIGN PATENT DOCUMENTS

| EP | 0293826 | 12/1988 |
| EP | 0406512 | 1/1991 |
| EP | 0940410 | 9/1999 |
| WO | WO9834958 | 8/1998 |
| WO | WO98/42754 | * 10/1998 |
| WO | WO 02068477 | 9/2002 |
| WO | WO 02083155 | 10/2002 |

OTHER PUBLICATIONS

Leali D et al., "Fibroblast growth Factor-2 antagonist activity and angiostatic capacity of sulfated *Escherichia coli* K5 polysaccharide derivatives," Journal of Biological Chemistry, Oct. 12, 2001, pp. 37900-37908, vol. 276, No. 41, XP001077702, ISSN: 0021-9258, abstract, American Society of Biological Chemists, Baltimore, MD, US; & 'Online! Journal of Biological Chemistry Papers in Press, Jul. 25, 2001, XP002226476, Retrieved from the Internet: <URL: http://www.jbc.org/cgi/content/abstract/M105163200v1> 'retrieved on Jan. 8, 2003! The whole document.
Casu Benito et al., "Heparin-like compounds prepared by chemical modification of capsular polysaccharide from E. coli K5," 1994, pp. 271-284, vol. 263, No. 2, ISSN: 0008-6215, cited in the application, abstract.

* cited by examiner

*Primary Examiner*—Shaojia Anna Jiang
*Assistant Examiner*—Ganapathy Krishnan
(74) *Attorney, Agent, or Firm*—Millen, White, Zelano & Branigan, P.C.

(57) ABSTRACT

The present invention relates to the use of N,O oversulfated K5 derivatives having a degree of sulfation higher than 3.2 or of their pharmaceutically acceptable salts for the preparation of pharmaceutical compositions for treating the infection and the consequent HIV/ADS disease.

15 Claims, No Drawings

USE OF OVERSULFATED POLYSACCHARIDES AS INHIBITORS OF HIV

SUBJECT OF THE INVENTION

The Acquired Immuno Deficiency Syndrome (AIDS) has become a global pandemia, even if the deaths caused by HIV infection are considerably decreasing in the countries with stable market economy where cocktails of specific inhibitors of the viral enzymes inverse transcriptase (RT) and protease entered in the clinical practice. About a dozen of drugs are nowadays available in the market. However, the treatment with such drugs is accomplished with heavy side effects. Furthermore, HIV-variants which are resistant to the drugs in use are emerging and diffusing. As, at the present time, retroviral therapy temporarily stops the viral replication but is not able to eradicate the HIV from the chronically infected cells, and, thus, from the seropositive individuals, it is essential to identify new classes of antiviral drugs which can complement and possibly substitute (in the case of pharmacological resistance) the drugs now in use.

Different steps of the replicative cycle of HIV are potentially vulnerable by specific inhibitors. These can be conventionally divided into:

A specific binding of the viral particle (virion) to the cell surface followed by the specific binding to the CD4+ cells by the interaction of the glycoprotein of the viral envelop (gp120 Env) exposed at the surface of the virion. The binding between gp120 Env and CD4 allows, through a conformational change, the subsequent binding of gp 120 Env with the co-receptors CCR5 and CXCR4 and the insertion of the fusogenic component of the viral envelop (gp41 Env) in the membrane of the target cell.

Early events subsequent to the virus entry, schematically subdividable into migration of the complex denominated of pre-integration from the cytoplasm to the nucleus contemporaneous to the retrotranscription process of the viral genoma from RNA to DNA, and, finally, to the integration of the viral DNA into the chromosomes of the infected cell (provirus).

Late events of the life cycle of HIV, which comprise the transcription of the viral genes to the synthesis of new viral proteins, their assembly to the internal surface of the cell, the gemmation of new virions that will detach from the infected cell to begin a new infection cycle.

The earliest phase of the infection process is the adhesion of the virion to the cell membrane that occurs independently from the interaction of gp120 Env with the specific receptors on the host cell. Among the different proposed mechanisms, the most reliable one involves the association of positively charged gp120 Env regions with the negatively charged membrane heparan sulfates (proteoglycans). In fact, the polyanions efficiently bind the gp120 Env molecule of many viral isolates and thus have potent antiviral effects in vitro and represent potential therapeutic agents.

Prior Art

It is known that the capsular polysaccharide K5 isolated from a *E. coli* strain (herein below simply referred to as "K5") described by W. F. Vann et al. (1981) in Eur. J Biochem. 116, 359-364, shows the same sequence as the biosynthetic precursor of heparin and heparan sulfate (N-acetylheparosan) and is chemically constituted by repetitive disaccharide units formed by D-glucuronic acid and N-acetylglucosamine linked α1-4, while the disaccharide units D-glucuronyl-N-acetylglucosamine are linked β1-4. The only difference, which is not important for the biological activities of K5 and its derivatives, between the heparin precursor N-acetylheparosan and K5 polysaccharide, is the presence of a double bond in position 4(5) at the non reducing end of some chains of the K5 polymer, as for instance described in EP 489647 and EP 544592 herein below mentioned.

After this first publication, other papers and patent applications described the preparation of the *E. coli* K5 polysaccharide having molecular weight ranges from few thousand to many hundred thousand Daltons and chemically or enzymatically modified K5 polysaccharides, for example to prepare N- and/or O-sulfated products or, possibly, N,O sulfated and epimerized in position 5 of the glucuronic acid to obtain heparin-like products. For example EP 333243, IT 1230785, EP 489647, EP 544592, WO 92/17507, WO 96/14425, WO 97/43317, WO 98/34958, WO 98/42754, WO 01/02597, and the paper of M. Manzoni et al. (1996), Journal Bioactive Compatible Polymers, 11, 301-311 are cited.

In particular, among these documents, EP 333243 describes O-sulfated K5 compounds possibly suitable in the treatment of pathologies due to viruses with an envelop like Herpes Symplex virus, vescicular stomatitis virus, type 1 HIV (HIV-1) and type 2 HIV (HIV-2). This document describes O-sulfated K5 polysaccharides having at most 1.25 sulfate groups per saccharide unit (correspondent to 2.5 sulfate groups per disaccharide), a tetrasaccharide, a hexasaccharide and an octasaccharide containing, respectively, 3.4, 3.2 and 1.5 sulfate groups per disaccharide unit.

Furthermore, WO 98/34958 describes O-sulfated derivatives of K5 polysaccharide having a sulfate/carboxyl ratio between 0.5 and 4 with antimetastatic and antiviral activity, in particular O-sulfated K5 having a degree of sulfation of from 2.5 to 4. According to this document, the most sulfated compounds (sulfate/disaccharide>2.5) show an interesting anti-HIV activity.

The N,O sulfated derivatives of K5 described in these references, in particular EP 489647, EP 544592 and WO 98/09636, have a degree of sulfation of from 1.6 to 3.1, while the degree of sulfation of O-sulfated K5 can reach 4. On the other hand, the activity of the known N,O sulfated K5 derivatives has never been described.

Casu et al. (1994) Carbohydrate Research, 263, 271-284 describe the N-deacetylation of K5, the N-sulfation and three methods of O-sulfation indicated as B, C and AC. According to method C, in which the sulfation of the N-sulfate K5 is performed using 10 mole equivalents of sulfating agent per free hydroxyl group at a temperature of 25-55° C. for a period of time ranging from 1 to 24 hours, polysulfated compounds are obtained after a further N-sulfation having a maximum sulfate/carboxyl ratio of 3.1.

Herein below the K5 derivatives are also designated as follow: "N-deacetylated K5" the N-deacetylated K5 polysaccharide, "N-sulfate K5" the N-deacetylated-N-sulfated K5 polysaccharide, "N,O-sulfated K5" the N-deacetylated-N,O-sulfated K5 polysaccharide and "N,O-oversulfated K5"0 the N-deacetylated-N,O-sulfated K5 polysaccharide with high degree of sulfation, obtainable according to the Method C of the above mentioned paper Casu et al.

The expression "O-oversulfation conditions" indicates condition of exhaustive O-sulfation, like that of the above mentioned Method C. By "degree of sulfation" the number of sulfate groups per disaccharide unit, expressed as sulfate/carboxyl ratio ($SO_3^-/COO^-$) is designated.

SUMMARY OF THE INVENTION

The invention is based on the hypothesis that by increasing the anionicity of the N,O sulfated polysaccharides from K5, N,O oversulfated K5 derivatives can be obtained with high anti-HIV activity, thus suitable for the treatment of the Acquired Immuno Deficiency Syndrome known as AIDS. Such an hypothesis, however, comes up against the problem that the N,O sulfation of the previously N-deacetylated K5 occurs with difficulty and, in fact, literature describes N,O sulfated polysaccharides from K5 with a degree of sulfation which does not reach 3.2.

It has now been found that, by purifying the K5 obtained by fermentation by treatment with isopropanol in a highly saline solution, a pure K5 polysaccharide substantially free of lipophilic substances is obtained and that, by submitting said K5 free of lipophilic substances to a N-deacetylation, N-sulfation, O-sulfation under O-oversulfation conditions, and optionally to a further N-sulfation, new N,O oversulfated K5 derivatives having a degree of sulfation higher than 3.2 are obtained.

These N,O oversulfated K5 derivatives are endowed with interesting activities of inhibition of the entry and of the replication of the HIV with a favourable ratio with respect to the global anticoagulant activity and, thus, they can be used for the preparation of pharmaceutical compositions for the treatment of HIV infections, in particular useful for combating the Acquired Immuno Deficiency at doses by which the risk of hemorrhagic side effects is extremely reduced.

More particularly, we have demonstrated that the N,O oversulfated K5 derivatives having a degree of sulfation higher than 3.2 have a high inhibitory effect on dualtropic viral strains that use both of the CCR5 and CXCR4 co-receptors (R5X4 strains) that are generated during the late phases of the HIV infection.

Said strains emerge in 50% of the seropositive individuals in the late phases of the infection and it is proven that they can cause a more accelerated progression of the pathology.

DETAILED DESCRIPTION OF THE INVENTION

The present invention relates to the use of N,O oversulfated K5 derivatives having a degree of sulfation higher than 3.2 or of their pharmaceutically acceptable salts for the preparation of pharmaceutical compositions for combating the infection and the consequent HIV/AIDS disease.

The N,O oversulfated K5 derivatives of the present invention exhibit a marked activity in suppressing the replication of various HIV-1 strains in primary CD4+ cells derived from peripheral venous blood of health seronegative adults isolated by Ficoll gradient, from the ring of which the fraction of mononucleate cells was obtained (PBMC) that are then stimulated with phytoagglutinin (PHA) for 3 days and subsequently maintained in a medium enriched with interkeukin-2 (IL-2) (PHA blasts). A second fraction of PBMC is submitted to a second gradient of Percoll to isolate the monocytes, that are seeded in adherence for 5-7 days to obtain in vitro derived macrophages (MDM) susceptible to the HIV infection.

In particular, the N,O sulfated K5 derivatives having a degree of sulfation higher than 3.2 have a high inhibitory effect on dualtropic strains R5X4 that are generated during the late phases of the HIV pathology. Said inhibitoy effect is also higher than that exerted by O-sulfated K5 derivatives with the same degree of sulfation such as those described in WO 98/34958.

Advantageously, the N,O oversulfated K5 used for such an use has a degree of sulfation of from 3.2 to 4, more advantageously from 3.5 to 4, preferably from 3.7 to 4.

Among the salts of said N,O oversulfated K5, sodium, potassium, calcium, magnesium, aluminum and zinc salts are the preferred.

The N,O oversulfated K5 derivatives of the invention preferably show mean molecular weights in the range of between about 2,000 and about 65,000, advantageously between 2,500 and 20,000 dalton (D). All the herein below indicated molecular weights are intended to be expressed in dalton and calculated according to Harenberg et al. Journal Chromatography (1983), 261, 287-292.

The N,O oversulfated K5 derivatives of the present invention are prepared by a process which comprises
  (a) treating a K5 from fermentation with isopropanol in a strong saline solution;
  (b) submitting the thus purified K5 to a N-deacetylation by alkaline hydrolysis and to a subsequent N-sulfation by treatment with a N-sulfating agent;
  (c) treating an ammonium salt of the N-sulfate K5 thus obtained with an O-sulfating agent in the O-oversulfation conditions;
  (d) if needed, submitting the product thus obtained to a N-sulfation and isolating the N,O oversulfated K5 as sodium salt which, if necessary, is converted into another salt.

In step (a), the K5 starting material can be one of the products obtained by fermentation of wild or cloned *Escherichia coli* strains, producing K5. In particular the K5 described in literature like those above cited can be used, advantageously those described by M. Manzoni et al., Journal Bioactive and Compatible polymers, 1996, 11, 301-311 and the one illustrated in PREPARATION I herein below.

More advantageously, the K5 starting material has a low molecular weight, in particular with a molecular weight distribution of from about 1,500 to about 15,000, preferably from about 2,000 to about 9,000, with a mean molecular weight of about 5,000, or a higher mean molecular weight, in particular with a distribution of from about 10,000 to about 50,000, preferably from about 20,000 to about 40,000, with a mean molecular weight of about 30,000. Preferably, the K5 starting material has a distribution of molecular weight of from about 1,500 to about 50,000 with a mean molecular weight of 20,000-25,000.

The molecular weight of K5 and of herein described derivatives thereof is intended as calculated using heparin fractions of known molecular weight as standards. The starting product can be a previously purified K5 from which, for example, the endotoxins, the pyrogens or other impurities have been eliminated by known methods.

Likely, if the K5 obtained at the end of step (a) is used for pharmaceutical purposes or for the preparation of N,O sulfated K5 for pharmaceutical use, it can be purified from pyrogens and endotoxins.

Practically, the starting K5 is dissolved in a 2-5 M saline solution, preferably of sodium chloride, at a concentration of from 0.5 to 10% and the thus obtained solution, brought to 2-4 M by a further addition of salt, preferably sodium chloride, is treated with 1-3 volumes of isopropanol at a temperature of 0-8° C.

After 1-18 hours at the same temperature, the product of step (a) completely precipitates and is isolated by filtration or centrifugation. If the purity of the product is not satisfactory, the procedure of step (a) is repeated. The solid product thus obtained is redissolved in water and recovered by ultrafiltration on a membrane.

At the end of step (a) a K5 having the same characteristics as those of the starting material, but being substantially free of lipophilic substances is obtained.

Practically, the K5 free of lipophilic substances is obtainable by a process which comprises (a1) treating a K5 from fermentation, dissolved in a 4 M solution of sodium chloride at 4° C. with 1 volume of isopropanol, (a2) bringing the saline solution to 3 M by adding the calculated amount of a sodium chloride saturated solution, (a3) keeping the solution at 4° C. overnight and (a4) isolating the product by centrifugation and eliminating the salts by ultrafiltration.

By the purification with isopropanol it is thus possible to obtain a K5 free of lipophilic substances with a purity higher than 99%. This K5 allows to obtain a high O-sulfation in the next step (c).

In step (b), the N-deacetylation is performed according to the known methods of alkaline hydrolysis, for example with hydrazine sulfate in hydrazine or with a base such as an alkaline hydroxide, for example sodium or potassium hydroxide, in water.

Preferably the reaction is performed in an aqueous solution of sodium hydroxide at a temperature of 40-80° C., by controlling the course of the reaction. In general, after at most 30 hours, but practically after 12-24 hours, the N-deacetylation is complete and the alkalinity of the medium is neutralized by treatment with an acid, preferably hydrochloric acid.

The solution containing the K5 and the salts is subsequently treated with a N-sulfating agent such as the adduct of a tertiary organic base with sulfuric anhydride (sulfur trioxide), such as pyridine sulfur trioxide ($C_5H_5N.SO_3$) or a trialkylamine sulfur trioxide such as trimethylamine sulfur trioxide in the presence of an alkaline carbonate such as sodium carbonate. The reaction can be performed at room temperature (20-30° C.), but it is also possible to work at higher temperatures (up to 65° C.) to shorten the reaction time. The addition of the alkaline carbonate and of the sulfating agent can be performed concurrently or the alkaline carbonate is introduced in bulk and the sulfating agent subsequently, stepwise, in a period of time which can last from 5 minutes to 12 hours. At the end of the reaction the mixture, at room temperature, is brought to pH 7.5-8 with an acid, preferably hydrochloric acid and the salts are eliminated for example by diafiltration. The so obtained solution, containing the N-sulfate K5 as an alkaline salt, can be passed to the subsequent step (c), or it can be concentrated and the N-sulfate K5 can be isolated as sodium salt with conventional methods. The thus obtained N-sulfate K5 is 90-100% sulfated.

In step (c) a solution containing the alkaline N-sulfate K5 as obtained in step (b) is passed on a cationic exchange resin, like IR 120 H$^+$ till acidic pH. The acidic solution so obtained is treated with a tertiary or quaternary organic base, for example with a trialkylamine like tributylamine, or with a tetraalkylammonium hydroxide, preferably tetrabutylammonium hydroxide reduced to the minimum volume and freeze dried. The thus isolated ammonium salt of the N-sulfate K5 is suspended in a polar aprotic solvent such as dimethylformamide or dimethylsulfoxide and treated with an O-sulfating agent, for example with the adduct $C_5H_5N.SO_3$. The adduct $C_5H_5N.SO_3$ can be used either in the solid state or in solution in the same polar aprotic solvent. The sulfation is performed at a temperature that can vary from the room temperature (20-30° C.) to 70° C., preferably from 40 to 60° C., for a period of time of from 2 to 24 hours.

At the end of the reaction, the solution at room temperature is treated with sodium chloride saturated acetone till complete precipitation. The precipitate is separated from the solvent by filtration, dissolved in the minimum amount of deionized water, for example 100 ml, and sodium chloride is added to the solution till 0.2 M concentration. The solution is brought to pH 7.5-8 with 2N sodium hydroxide and treated with acetone till complete precipitation. After filtration the solid is dissolved in 100 ml of deionized water and purified from the residual salts by ultrafiltration as described in step (b).

If from the analysis by $^{13}$C-NMR of a freeze dried sample of the thus obtained product it appears that a partial N-desulfation occurred during the oversulfation, the product is submitted to step (d).

In step (d) the product obtained at the end of step (c) is treated with a N-sulfating agent by operating under the conditions of step (b) till complete N-sulfation, repeating the procedure if the N-sulfation is not complete.

The N,O oversulfated K5 thus obtained is isolated as sodium salt, that can be converted into another salt, like potassium, calcium, magnesium, aluminum, zinc or complex salts by known methods, for example by ionic exchange with a suitable resin, by precipitation with solvents or by ultrafiltration through membranes.

The purity of the new purified K5 from fermentation can be assayed by $^1$H-NMR spectrum, by UV spectrum, by carbazole reaction, or by a kit for the protein determination. By these assays it was demonstrated that the K5 obtained at the end of step (a) has, as the essential characteristic, a $^1$H-NMR spectrum in which signals in the field below 1.5 ppm are absent. Moreover the nucleic acids are not detectable, (absorbance 0 at 260 nm with a standard UV spectrophotometer) and the proteins are not higher than 0.5%, advantageously below 0.25%, more advantageously below 0.1%, preferably below 0.03% according to BioRad kit.

Actually, the new pure K5 obtained at the end of step (a) is free from lipophilic substances and nucleic acids. The use of "substantially", referred to the absence of lipophilic substances and of "not detectable" referred to the nucleic acids takes in account the sensitivity of the instruments used which did not reveal the presence of the above mentioned impurities.

Thus it was established that the $^1$H-NMR spectrum of the pure K5 polysaccharide obtained in this way lacks the signals at <1.5 ppm characteristic of the methyl group of lipophilic substances.

The new thus purified K5 compounds, which allow the preparation of N,O oversulfated K5 with a high degree of sulfation, have preferably a low molecular weight, in particular with a distribution of from about 1,500 to about 15,000, preferably from about 2,000 to about 9,000, with a mean molecular weight of about 5,000, or a higher molecular weight, in particular with a distribution of from about 10,000 to about 50,000, preferably from about 20,000 to about 40,000 with a mean molecular weight of about 30,000. Preferably the K5 starting material has a molecular weight distribution of from about 1,500 to about 50,000 with a mean molecular weight of 20,000-25,000.

The N,O oversulfated K5 derivatives obtained according to the above mentioned process, especially in their pharmaceutically acceptable form, are highly anionic products useful for the preparation of pharmaceutical compositions with antiviral activity, in particular suitable for the treatment of the HIV infection and of AIDS that is its consequence.

Said N,O oversulfated K5 derivatives have a degree of sulfation higher than 3.2, advantageously from 3.2 to 4, more advantageously from 3.5 to 4, preferably from 3.7to 4.

Advantageously said N,O oversulfated K5 have a low molecular weight, in particular with a distribution of from about 2,000 to about 16,000, preferably from about 2,500 to about 10,000 with a mean molecular weight of about 6,500, or a somewhat higher molecular weight, in particular with a distribution of from about 13,000 to about 65,000, preferably from about 25,000 to about 50,000 with a mean molecular weight of about 40,000. Preferably the N,O oversulfated K5 starting material of the present invention has a molecular weight distribution of from about 2,000 to about 65,000, with a mean molecular weight of 25,000-30,000. Also N,O oversulfated K5 having a very low mean molecular weight, for example of from about 2,000 to 5,000, obtained by depolymerization, constitute very interesting products.

The depolymerization that allows the preparation of the N,O oversulfated K5 derivatives with mean molecular weight of from 2,000 to 5,000 can be performed at the end of one of steps (b)-(d) of the process illustrated above, preferably at the end of step (b) or on the final N,O oversulfated K5.

The depolymerization can be performed according to anyone of the known methods for the depolymerization of heparin, for example by nitrous acid and subsequent reduction with sodium borohydride (EP 37319), by periodate (EP 287477), by free radicals (EP 121067) or by β-elimination (EP 40144). In the case of N,O oversulfated K5 the depolymerization is advantageously performed on a N-sulfate K5 obtained at the end of step (b) with nitrous acid and subsequent reduction with sodium borohydride as detailed in EP 544592. At the end of the depolymerization and reduction, the low molecular weight product thus obtained is submitted to steps (c) and, optionally, (d) and the N,O oversulfated K5 is isolated.

Alternatively, the same procedure of depolymerization and reduction can be applied to a N,O oversulfated K5 with high molecular weight and the corresponding low molecular weight product is obtained.

Among the salts of the above mentioned N,O oversulfated K5 derivatives sodium, potassium, calcium, magnesium, aluminum and zinc salts are the preferred.

The drugs nowadays used for the therapy of the HIV infection interfere in two fundamental phases of the life cycle of the virus: the retrotranscription and the decomposition of the polyprotein Gag in its mature forms by the viral protease. Because of the discovery of the chemokine receptors CCR5 and CXCR4 as obliged co-receptors of HIV for the infection of lymphocytes and macrophages CD4+, a potential new class of antiviral drugs comprises molecules able to inhibit the binding of the virus to the CD4 molecule and/or to the chemokine receptor and/or to inhibit the process of fusion of the viral and cellular membranes mediated by the envelop glycoprotein gp41 (Moore J P, and Stevenson M, Nat Rev Mol Cell Biol 2000, 1:40-49). In this context, the development of inhibitors of the entry of dualtropic viruses R5X4, thus able to infect the CD4+ cells interacting with CCR5 or CXCR4, has a great relevance in preventing the evolution of HIV-1 of the B group, dominant in USA, Canada, Australia and Europe, the evolution being associated to an accelerated progression of the pathology (Koot M., et al., Ann. Intern. Med. 1993, 118:681-688). The anti HIV activity was tested on the HIV-1 virus both on PHA blasts (blasts) and on macrophages derived from the adhesion of monocytes (MDM) of peripheral blood. The viral strain HIV-1$_{Bal}$, using only the co-receptor CCR5 was used both for the infection of blasts and of MD, while the dualtropic strain using the co-receptor CXCR4 beside the CCR5 (R5X4 virus) and the strain using the co-receptor CXCR4 only (X4 strain) were used just for the infection of the blasts. These strains (R5X4 and X4) are generated during the late phases of the infection, the virus can extend its infective capacity to cells expressing the receptor CXCR4 beside the CCR5.

The viruses are added to the multiplicity of the infection (m.o.i.: number of infective viral units/number of target cells) of 0.1. Aliquots of supernatants of the cultures are collected every 48-72 hours arid the RT viral activity present in the supernatant of the culture is tested as described by Vicenzi et al. (J. Virol. 73:7515-7523, 1999). As the RT enzyme is 99% associated to the virions, the determination of its activity is equivalent to the determination of the presence of viral particles in said fluid. The RT activity reaches a peak and then decreases because of the cytopatic effect of the virus on the target cells. The peak of RT activity is then used as an index to evaluate the concentration of the potential antiviral agent.

The N,O oversulfated K5 obtained according to the PREPARATION III, representative of the present invention, having a degree of sulfation of 3.84 and designated K5 N,OS(H), was compared with two other derivatives of K5 polysaccharide, in particular with a N,O sulfated K5 having a degree of sulfation of 1.77 and designated K5 N,OS(L), obtained as described in PREPARATION V, and with an O-sulfated K5 having a degree of sulfation of 3.77, designated K5 OS(H) and prepared as described in PREPARATION VI.

The HIV-1 replication both in PHA blasts and in MDM is inhibited by the compounds tested in vitro at concentrations in the range between 1 and 100 µg/ml.

However, the representative compound of the present invention, K5-N,OS(H), inhibits the dualtropic strains R5X4 that generate during the advanced steps of the infection for 99% already at 1 µg/ml concentration, while the two reference products, K5-OS(H) and K5 N,OS(L), inhibit the same strains for 98% at the concentration of and 100 µg/ml, respectively. Furthermore the K5 N,OS(H), as much as the K5 OS(H), is active on all the other strains used at concentrations of 1-10 µg/ml, showing to be always more active than K5 N,OS(L).

For the foreseen therapeutic uses the above mentioned N,O oversulfated K5 derivatives and their salts thereof are formulated according to conventional techniques in suitable administration forms such as sterile solutions, topical dosage forms and, in general, in all those forms proposed till today for polysaccharide or glycosaminoglycan derivatives. Also the therapeutic doses are chosen in analogy with those already studied for the known natural compounds.

The administration of the N,O oversulfated K5 can occur by oral, transdermal or, preferably, parenteral route, in particular subcutaneous, intramuscular or intravenous or topical route.

In humans, the daily dose for the parenteral administration is foreseen as 0.5-500 mg/Kg/day, advantageously 5-250 mg/Kg/day, preferably 10-150 mg/Kg/day, while the dose foreseen by topical route is 1-1000 mg/Kg/day, advantageously 10-500 mg/Kg/day, preferably 20-100 mg/Kg/day.

For their administration, the N,O oversulfated K5 derivatives having a degree of sulfation higher than 3.2, advantageously from 3.2 to 4, more advantageously from 3.5 to 4, preferably from 3.7 to 4, or their salts, constitute thus active ingredients that are formulated in pharmaceutical compositions suitable for the treatment of the HIV infections, in particular of the Acquired Immuno Deficiency Syndrome.

Thus, according to another of its aspects, the present invention provides a pharmaceutical composition for the treatment of the HIV infection which comprises, as an active ingredient thereof, a pharmacologically effective amount of a N,O oversulfated K5 having a degree of sulfation higher than 3.2 or of one its pharmaceutically acceptable salts, in admixture with a pharmaceutical vehicle or excipient.

Said N,O oversulfated K5 can have one of the above illustrated characteristics of degree of sulfation.

A salt selected from the group consisting of sodium, potassium, calcium, magnesium, aluminum and zinc salts constitutes a suitable active ingredient of the compositions of the present invention.

In the pharmaceutical compositions of the present invention for the oral, subcutaneous, intravenous, transdermal, or topical administration, the active ingredients are preferably administered in dosage unit form, in admixture with the classical pharmaceutical excipients or vehicles. The dose can amply change in function of age, weight, and health conditions of the patient, as much as the of severity of the infection and of the route of administration. This dose comprises the administration of a dosage unit from 1 to 1,000 mg, advantageously from 10 to 750 mg, preferably from 250 to 500 mg of active ingredient, from one to three times per day by intravenous, subcutaneous, oral, transdermal or topical route.

Finally, according to one of its further aspects, the present invention provides a method for the treatment of the HIV infection, which comprises administering to a patient in need of such a treatment an effective amount of a N,O oversulfated K5 having a degree of sulfation higher than 3.2, advantageously from 3.2 to 4, more advantageously from 3.5 to 4, preferably from 3.7 to 4 or of one of its pharmaceutically acceptable salts.

Particularly advantageous N,O oversulfated K5 derivatives are those having the above illustrated molecular weight distributions and the mean molecular weights.

The method for treating the HIV infection comprises also the administration of the above illustrated pharmaceutical compositions, advantageously those of claims 14-24.

The invention also provides a method for treating the HIV infection, in which said treatment is performed by administering to the patient a pharmaceutical composition formulated with diluents or pharmaceutically acceptable carriers for parenteral administration or topical application. Advantageously, for the parenteral administration a dosage of from 0.5 to 500 mg/Kg/die and for the topical administration a dosage of from 1 to 1,000 mg/Kg/die are provided.

The following examples illustrate the invention.

Preparation I

Preparation of the K5 Polysaccharide from *Escherichia coli*

First a fermentation in flask using the following medium is performed:
Defatted soy 2 g/l
$K_2HPO_4$ 9.7 g/l
$KH_2PO_4$ 2 g/l
$MgCl_2$ 0.11 g/l
Sodium citrate 0.5 g/l
Ammonium sulfate 1 g/l
Glucose 2 g/l
Water 1,000 ml
pH=7.3.

The medium is sterilized at 120° C. for 20 minutes. The glucose is prepared separately as a solution which is sterilized at 120° C. for 30 minutes and sterile added to the medium. The flask is inoculated with a suspension of *E. coli* cells Bi 8337/41 (O10:K5:H4) from a slant maintained in Tryptic soy agar, and incubated at 37° C. for 24 hours under controlled stirring (160 rpm, 6 cm of run). The bacterial growth is measured counting the cells with a microscope. In a further step, a Chemap-Braun fermentor with a volume of 14 liters containing the same medium above is inoculated with the 0.1% of the above flask culture and the fermentation is performed with 1 vvm aeration (vvm=air volume per liquid volume per minute), 400 rpm stirring and temperature of 37° C. for 18 hours. During the fermentation pH, oxygen, residual glucose, produced K5 polysaccharide and bacterial growth are measured. At the end of the fermentation the temperature is raised to 80° C. for 10 minutes. The cells are separated from the medium by centrifugation at 10,000 rpm and the supernatant is ultrafiltrated through a SS316 (MST) module equipped with PES membranes with a nominal cut off of 800 and 10,000 D to reduce the volume to ⅕. Then K5 polysaccharide is precipitated adding 4 volumes of acetone at 4° C. and left to sediment for one night at 4° C. and finally is centrifuged at 10,000 rpm for 20 minutes or filtrated. Then a deproteinization using a protease of the type II from *Aspergillus Orizae* in 0.1M NaCl and 0.15 M ethylenediaminotetracetic acid (EDTA) at pH 8 containing 0.5% sodium dodecyl sulfate (SDS) (10 mg/l of filtrate) at 37° C. for 90 minutes is performed. The solution is ultrafiltrated on a SS 316 module with a nominal cut off membrane of 10,000 D with 2 extractions with 1M NaCl and washed with water until the absorbance disappears in the ultrafiltrate. K5 polysaccharide is then precipitated with acetone and a yield of 850 mg /1 of fermentor is obtained. The purity of the polysaccharide is measured by uronic acid determination (carbazole method), proton and carbon NMR, UV and protein content. The purity is higher than 80%.

The so obtained polysaccharide is composed of two fractions with different molecular weight, 30,000 and 5,000 D respectively as obtained from the HPLC determination using a 75 HR Pharmacia column and one single fraction with retention time of about 9 minutes using two columns of Bio-sil SEC 250 in series (BioRad) and $Na_2SO_4$ as mobile phase at room temperature and flow rate of 0.5 ml/minute. The determination is performed against a curve obtained with heparin fractions with known molecular weight.

The $^1$H-NMR spectrum of thus obtained K5 shows that in the region below 1.5 ppm many signals attributable to the methyl groups of lipophilic substances are present.

Preparation II

Preparation of a K5Free from Lipophilic Substances

In 100 ml of an aqueous solution containing 4M sodium chloride and thermostated at 4° C. are dissolved 5 gr of the K5 obtained at the end of PREPARATION I and 1 volume of cold isopropanol is added to the thus obtained solution. The salt concentration of the solution is brought to 3 M adding a calculated amount of a saturated solution of sodium chloride and the cooled solution is kept at cold temperature (about 4° C.) overnight. The precipitate formed is separated by centrifugation at 10,000 rpm for 20 minutes and the purity of the product is controlled by dialysis for one night and subsequent $^1$H-NMR analysis from which the signals in the region below 1.5 ppm are absent. If necessary, the procedure of dissolution in water containing 4M NaCl and precipitation with isopropanol is repeated. The precipitate is dissolved in water and ultrafiltrated on a Miniplate membrane Millipore with a 10,000 D cut off till disappearance of the salts. A K5 having a purity of at least 99% and whose $^1$H-NMR spectrum there are no traces of lipophilic impurities in the region below 1.5 ppm.

The protein content calculated using BioRad kit is 0.02% and the nucleic acids are not detectable (absorbance 0 at 260 nm).

Preparation III

Preparation of a N,O oversulfated K5

(i) N-deacetylation

Ten grams of pure K5 polysaccharide prepared as described in PREPARATION I and purified as described in PREPARATION II are dissolved with 1,000 ml of 2 N sodium hydroxide and the solution thus prepared is kept at 60° C. for 24 hours. The solution is brought to room temperature and then to neutral pH with 6N hydrochloric acid.

(ii) N-sulfation

To the solution containing the deacetylated K5, kept at 40° C., 16 g of sodium carbonate and subsequently 16 gr of pyridine sulfur trioxide in 4 hours are added. At the end of the reaction, after 24 hours, the solution is brought to room temperature and then to pH 7.5-8 with a 5% solution of hydrochloric acid. The product is purified from salts by diafiltration using a spiral membrane of 1,000 D (Prepscale Cartridge-Millipore). The process is ended when the conductivity of the permeate is below 1,000 μS, preferably below 100 μS. The intradialysis is reduced till a polysaccharide concentration of 10% using the same dialysis system in concentration. The concentrated solution is freeze dried. The analysis of the $^{13}$C-NMR does not show N-acetyl or NH2 residual groups.

(iii) O-oversulfation

The lyofilized product obtained at the end of step (ii) is dissolved in 100 ml of deionized water and the solution is brought to 10° C. with a cooling bath then passed onto a cationic exchange resin IR120H+ (100 ml). Both the column and the reservoir are kept at 10° C. After the passage of the solution containing the sample the resin is washed with deionized water till the pH of the permeate is higher than 6 (about 3 volumes of deionized water). The acidic solution is brought to neutrality (pH 7) with tetrabutylammonium hydroxide (15% aqueous solution), then reduced to the minimum volume and freeze dried. The tetrabutylammonium salt is dissolved in 400 ml of dimethylformamide and added with 35 g of $C_5H_5N.SO_3$ in solid form. The solution is kept at 50° C. for 24 hours. At the end of the reaction the solution is cooled to room temperature and added with 3 volumes of sodium chloride saturated acetone, cooled to 4° C. till complete precipitation (12 hours). The precipitate is separated from the solvent by filtration, solubilized with the minimum amount of deionized water (about 100 ml) and to the solution sodium chloride till 0.2 M concentration is added.

The solution is brought to pH 7.5-8 with 2N sodium hydroxide and treated with 2 volumes of acetone till complete precipitation. The precipitate is separated from the solvent by filtration. The solid obtained is solubilized with 100 ml of deionized water and purified from the residual salts by ultrafiltration as described in step (ii) using a spiral membrane of 1,000 D (Prepscale Cartridge Millipore).

(iv) N-sulfation

The solution thus obtained, containing the O-sulfated product, is treated as previously described in step (ii) for the N-sulfation. The product shows a mean molecular weight of 15,000 D and a sulfate/carboxyl ratio of 3.84. The distribution of the sulfate groups, determined with the $^{13}$C-NMR is the following: the glucosamine unit of the constitutive disaccharide is 100% N-sulfated and 6-O sulfated, while, as for the glucuronic units, 30% are mono O-sulfated and 70% are O-disulfated.

Preparation IV

Preparation of a N,O oversulfated K5

By operating as described in PREPARATION III starting from a K5 obtained and characterized as described by M. Manzoni et al. (1996), purified as described in PREPARATION II, a N,O oversulfated K5, designated K5-N,OS(H1), having mean molecular weight of 13,000 and a sulfate to carboxyl ratio of 3.54 is obtained.

Preparation V

Preparation of a N, O sulfated K5

By operating as described in PREPARATION 1 ml, but using 7 g of adduct $C_5H_5N.SO_3$ in step (iii), a N,O sulfated K5 designated K5-N,OS(L) is obtained, having a mean molecular weight of 14,000 and a sulfate to carboxyl ratio of 1.7.

Preparation VI

Preparations of a O-oversulfated K5

By operating as described in step (iii) of PREPARATION III on a K5 obtained as described in PREPARATION I and purified as described in PREPARATION II, an O-oversulfated K5, designated as K5-OS(H), having a mean molecular weight of 18,000 and a sulfate/carboxyl ratio of 3.77 is obtained.

EXAMPLE 1

The anti-HIV activity was tested on PHA blasts (blasts) using the viral strain HIV-1$_{Bla}$, able to use only the co-receptor CCR5 (monotropic virus R5).

A N,O oversulfated K5 representative of the present invention, the K5 N,OS(H) obtaining according to PREPARATION III, and having a degree of sulfation of 3.84 was compared with other two derivatives of K5 polysaccharide, in particular with a N,O sulfated K5 having a degree of sulfation of 1.77 and designated K5 N,OS(L), obtained as described in PREPARATION V, and with a O sulfated K5 having a degree of sulfation of 3.77 designated K5 OS(H) and prepared as described in PREPARATION VI. The results of the effects of the three K5 derivatives on the infection of cells obtained from a single donor and tested in triplicate for each derivative concentration, representative of those obtained in isolated cells from three independent donors, are reported in Table 1. All the three tested samples reach the maximum inhibition of RT at the concentration of 10 μg/ml.

TABLE 1

| Concentration (μg/ml) | K5 OS(H) | K5 N,OS(H) | K5 N,OS(L) |
|---|---|---|---|
| 0.1 | 62.5 | 30.7 | 4.8 |
| 1 | 81.2 | 40.8 | 31.3 |
| 10 | 98.5 | 96 | 98.7 |
| 100 | 98.9 | 99 | 99 |

EXAMPLE 2

The products under examination were tested on PHA blasts using the viral strain HIV-1$_{LAV/IIIB}$ which uses only the co-receptor CXCR4 (monotropic virus X4).

The strain X4 can generate, even if rarely, during the late phases of the infection before the evolution of the pathology to clear AIDS.

The results reported in Table 2, show that at the concentration of 10 μg/ml, both K5 OS(H) and K5 N,OS(H) inhibit almost completely the RT activity. At the concentration of 1 μg/ml, the K5 OS(H) inhibits almost completely the RT activity, while K5 N,O(H) inhibits for the 55%.

TABLE 2

| Concentration (μg/ml) | K5 OS(H) | K5 N,OS(H) | K5 N,OS(L) |
|---|---|---|---|
| 0.1 | 44.8 | 28.5 | 30 |
| 1 | 99.2 | 55 | 31.8 |
| 10 | 99.1 | 98.9 | 85.1 |
| 100 | 99.2 | 98.7 | 98.7 |

EXAMPLE 3

The products under examination were tested on blasts by using the viral strain HIV-1 89.6 which uses both the co-receptor CCR5 and CXCR4 (dualtropic viruses R5X4). The dualtropic strains R5X4 can generate during the late phases of the infection in about 50% of the infected individuals by HIV-1 of B group, and can derive both from a mixture of monotropic species R5 and X4 and from viruses able to use simultaneously both the receptors. (S. Ghezzi et al. Virology, 280:253-261, 2001).

The results are reported in Table 3 which shows how K5 N,OS(H) inhibits almost completely the RT activity at the concentration of 1 μg/ml, while K5 OS(H), at this concentration, has a very low activity, at least lower than that of K5 N,OS(L).

TABLE 3

| Concentration (μg/ml) | K5 OS(H) | K5 N,OS(H) | K5 N,OS(L) |
|---|---|---|---|
| 0.1 | 15.77 | 14.4 | 40.3 |
| 1 | 25 | 96.1 | 56 |
| 10 | 97.1 | 96.7 | 68.8 |
| 100 | 99 | 98.7 | 77.9 |

EXAMPLE 4

The anti-HIV activity was tested on the HIV-1 virus on macrophages derived from monocytes of peripheral blood (MDM), infected with the viral strain HIV-1$_{Bal}$ which uses only the co-receptor CCR5 (monotropic virus R5).

The results of RT inhibition are reported in table 4 where K5 OS(H) and K5 N,OS(H) are substantially equipotent, while K5 N,OS(L) has a very low activity.

TABLE 4

| Concentration (μg/ml) | K5 OS(H) | K5 N,OS(H) | K5 N,OS(L) |
|---|---|---|---|
| 0.1 | 41 | 30.7 | 39.5 |
| 1 | 61.9 | 40.8 | 44.3 |
| 10 | 94.1 | 96 | 40.1 |
| 100 | 95.8 | 99 | 46.4 |

The invention claimed is:

1. A method for combating or treating an HIV infection in a subject in need thereof comprising administering to said subject an effective amount of a N,O oversulfated K5 polysaccharide having a sulfation degree of 3.2 to 4, or a salt thereof.

2. A method according to claim 1, wherein said N,O oversulfated K5 polysaccharide has a sulfation degree of 3.5 to 4.

3. A method according to claim 2, wherein said N,O oversulfated K5 polysaccharide has a sulfation degree of 3.7 to 4.

4. A method according to claim 1, wherein said HIV infection is the sole cause of the Acquired Immuno Deficiency Syndrome called AIDS.

5. A method according to claim 1, wherein said N,O oversulfated KS polysaccharide is in the form a pharmaceutically acceptable salt thereof.

6. A method according to claim 5, wherein said pharmaceutically acceptable salt is a sodium, potassium, calcium, magnesium, aluminum or zinc salt of said N,O oversulfated K5 polysaccharide.

7. A method according to claim 1, wherein said N,O oversulfated K5 polysaccharide has a molecular weight with a distribution of about 2,000 to about 16,000.

8. A method according to claim 7, wherein said distribution is of about 2,500 to about 10,000, with a mean molecular weight of about 6,500.

9. A method according to claim 1, wherein said N,O oversulfated K5 polysaccharide has a molecular weight with a distribution of about 13,000 to about 65,000.

10. A method according to claim 9, wherein said distribution is about 25,000 to about 50,000, with a mean molecular weight of 40,000.

11. A method according to claim 1, wherein said N,O oversulfated K5 polysaccharide has a molecular weight with a distribution of about 2,000 to about 65,000, with a mean molecular weight of 25,000-30,000.

12. A method according to claim 1, wherein said N,O oversulfated K5polysaccharide is obtained by depolymerization and has a mean molecular weight of 2,000 to 5,000.

13. A method according to claim 1, wherein said N,O oversulfated K5 polysaccharide is formulated in a pharmaceutical composition in admixture with one or more pharmaceutically acceptable carriers or diluents suitable for parenteral administration or topical application.

14. A method according to claim 13, wherein a daily dosage of 0.5 to 500 mg/kg is used for the parenteral administration.

15. A method according to claim 13, wherein a daily dosage of 1 to 1,000 mg/Kg is used for the topical application.

* * * * *

UNITED STATES PATENT AND TRADEMARK OFFICE
CERTIFICATE OF CORRECTION

PATENT NO. : 7,268,122 B2 Page 1 of 1
APPLICATION NO. : 10/484883
DATED : September 11, 2007
INVENTOR(S) : Guido Poli It is certified that error appears in the above-identified patent and that said Letters Patent is hereby corrected as shown below:

Column 14, line 28, reads "oversulfated KS" should read -- oversulfated K5 --

Signed and Sealed this

Eighth Day of April, 2008

JON W. DUDAS
*Director of the United States Patent and Trademark Office*